US00RE39021E

(19) United States
(12) Reissued Patent
Sweeny

(10) Patent Number: US RE39,021 E
(45) Date of Reissued Patent: Mar. 21, 2006

(54) HYDANTOIN-ENHANCED HALOGEN EFFICACY IN PULP AND PAPER APPLICATIONS

(75) Inventor: Philip G. Sweeny, Hackettstown, NJ (US)

(73) Assignee: Lonza Inc., Fair Lawn, NJ (US)

(21) Appl. No.: 10/044,594

(22) Filed: Jan. 10, 2002

Related U.S. Patent Documents

Reissue of:
(64) Patent No.: 5,565,109
Issued: Oct. 15, 1996
Appl. No.: 08/323,459
Filed: Oct. 14, 1994

(51) Int. Cl.
*C02F 1/50* (2006.01)

(52) U.S. Cl. ..... 210/755; 162/161; 210/754; 210/756; 210/764

(58) Field of Classification Search ..... 162/161; 210/754, 755, 756, 764
See application file for complete search history.

(56) References Cited

U.S. PATENT DOCUMENTS

| | | | | | |
|---|---|---|---|---|---|
| 3,328,294 | A | * | 6/1967 | Self et al. | 210/744 |
| 3,749,672 | A | * | 7/1973 | Golton et al. | 252/186.34 |
| 4,297,224 | A | * | 10/1981 | Macchiarolo et al. | 210/755 |
| 4,427,692 | A | * | 1/1984 | Girard | 514/390 |
| 4,537,697 | A | * | 8/1985 | Girard | 510/192 |
| 4,698,165 | A | * | 10/1987 | Theyson | 210/755 |
| 4,925,866 | A | * | 5/1990 | Smith | 514/389 |
| 5,565,109 | A | * | 10/1996 | Sweeny | 210/755 |
| 5,976,386 | A | | 11/1999 | Barak | 210/756 |
| 6,132,628 | A | | 10/2000 | Barak | 210/756 |

FOREIGN PATENT DOCUMENTS

| | | | |
|---|---|---|---|
| GB | 1358617 | * | 7/1974 |
| JP | 56-31492 | * | 3/1981 |
| WO | WO 96/10541 | | 4/1996 |

OTHER PUBLICATIONS

Chemical Abstract No. 30168q, 1990.*
Feb. 28, 1997, Label for Lonza, Inc.'s DANTOBROM, EPA Reg. No. 6836–117.*
Feb. 28, 1997, Label for Lonza, Inc.'s DANTOBROM, EPA Reg. No. 6836–115.*
Feb. 1, 1982, 1982 Annual Meeting of Cooling Tower Institute Article, (Matson).*

* cited by examiner

*Primary Examiner*—Peter A. Hruskoci
(74) *Attorney, Agent, or Firm*—Darby & Darby

(57) ABSTRACT

Free halogen sources (e.g., sodium hypochlorite and chlorine) added as slimicides in high organic component process streams such as pulp and paper processing are rendered more efficacious by the addition of selected N-hydrogen compounds (namely, 5,5-dimethylhydantoin, 5-ethyl-5-methylhydantoin, cyanuric acid, succinimide, urea, 4,4-dimethyl-2-oxazolidinone, and glycouril) to the process stream. The latter compounds may be added to the process stream before or after the slimicide is added or combined with the slimicide and added directly thereto. The direct use of halogenated hydantoins has also been found to provide improved efficacy relative to free halogen sources. In addition, absorbable organic halogen by-products are reduced.

9 Claims, No Drawings

HYDANTOIN-ENHANCED HALOGEN EFFICACY IN PULP AND PAPER APPLICATIONS

Matter enclosed in heavy brackets [ ] appears in the original patent but forms no part of this reissue specification; matter printed in italics indicates the additions made by reissue.

BACKGROUND OF THE INVENTION

Sodium hypochlorite and chlorine gas are commonly used as circulating water slimicides. Upon reaction with organic system components, these materials can produce adsorbable organic halogen (AOX) by-products which are environmentally undesirable. In addition, the bactericidal efficacy of these materials is substantially reduced in high organic component systems because of rapid reactions of free halogen with organic materials. In high organic component recirculating waters such as pulp and paper processing and oil field applications, these deleterious effects are pronounced.

U.S. Pat. No. 3,328,294 teaches reaction of sulfamic acid with hypochlorite solutions, forming N-chlorosulfamate solutions which are used to disinfect paper-processing streams. The stated advantage is reduced reactions with paper-processing components. Enhanced biocidal efficacy is demonstrated over a non-oxidizing biocide containing N-methyldithiocarbamate and cyanodithioimidocarbonate with bacterial concentrations of $10^3$ cfu/ml being achieved at residual chlorine concentrations of 1.6 ppm as $Cl_2$. Unfortunately, as a practical matter, N-chlorosulfamic acid provides reduced biocidal efficacy relative to hypochlorite, thus limiting its usefulness as a papermaking slimicide.

U.S. Pat. No. 3,749,672 teaches the use of N-hydrogen materials to formulate bleaching solutions with enhanced stability to spontaneous decomposition. The claimed formulations contains (A) to hypohalite, (B) an N-hydrogen compound, (C) N-halo relation product of (A) with (B) at concentrations of $1.0\times10^{-3}$ to 1.0 molar, and (D) a buffer to maintain pH 4–11. The preferred compositions are liquid formulations containing a phosphate buffer, sulfamic acid and sodium hypochlorite buffered at pH 10. Use of such formulations containing the N-hydrogen compounds is discussed, as is fighting microorganisms in paper mills. The essence of the invention is the production of stable formulations which can be handled and shipped without the loss of active halogen. This is effected by the incorporation of a buffer. The invention is not concerned with the on-site combination of hypochlorite-containing solutions or process streams with N-hydrogen compounds, but only with shelf-stable formulations.

While this patent teaches reduced yellowing when the formulations are used as bleaches, neither the reduction of AOX nor the unexpected biocidal activity enhancement of active halogen by N-hydrogen compounds in pulp slurries is revealed.

BRIEF DESCRIPTION OF THE INVENTION

It has been discovered that selected N-hydrogen compounds and their chlorinated derivatives, such as 5,5-dimethylhydantoin (DMH), dramatically improve the bactericidal efficacy of hypochlorite solutions in pulp slurries, significantly reducing the amount of hypochlorite required to achieve biological control. Minimization of chlorine usage reduces the predisposition for AOX formation, as well as enhancing cost-effectiveness.

The efficacy is believed to result from the conversion of free halogen to combined halogen by DMH. DMH effectively increases the lifetime of active halogen, thereby increasing biocidal efficacy. Such action increases cost effectiveness and reduces AOX formation.

In contrast to the teaching of U.S. Pat. No. 3,749,672, the subject invention avoids the need to preformulate the constituents off-site and to buffer the solution. On-site formulation of active halogen:N-hydrogen mixtures allows for site-specific stoichiometric optimization in the system recirculation water. The relative stabilities of active halogen and N-hydrogen compounds in recirculation systems is site-specific, since they depend on such factors as composition, temperature, and degree of recycle. Modification of the active halogen:N-hydrogen ratio is not possible with the preformulated solutions of the prior art. Secondly, on-site formulation eliminates the expense and burdens of adding a buffer.

In another embodiment of the instant invention, it has been discovered that certain halogenated N-hydrogen compounds per se also serve as outstanding slimicides for the treatment of circulating water containing organic matter such as in the pulp and paper industry. These compounds show enhanced efficacy over the hypochlorite in these applications. This result is particularly surprising since organic matter, generally over 0.2 wt. % and frequently over 0.5 wt. %, would be expected to interfere with the biocidal efficacy of such compounds. Typically these processing streams have from 0.2 to 3 wt. % organic matter, most frequently from 0.5 to 2 wt. %, comprised of approximately 95–99% pulp fiber as well as additional materials such as sizing rosin and starch.

The N-halohydantoin compounds useful in this embodiment of the invention have the formula:

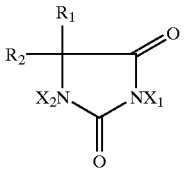

$R_1$ and $R_2$ are independently selected from hydrogen and alkyl groups (having from 1 to 12 carbons), and $X_1$ and $X_2$ are independently selected from bromine, chlorine and hydrogen, at least one of $X_1$ and $X_2$ being halogen, with the proviso that, when $X_1$ or $X_2$ is bromine, $R_1$ is methyl and $R_2$ is ethyl. In preferred embodiments, $R_1$ is methyl and $R_2$ is either methyl or ethyl. Preferred halohydantoins include 1,3-dichloro-5,5-dimethylhydantoin; 1-chloro- 5,5-dimethylhydantoin; and dibromo- and bromochloroethylmethylhydantoins; and combinations of these derivatives. Another preferred embodiment includes a mixture of chloro derivatives of 5-ethyl-5-methylhydantoin, such as the mixtures currently sold under the trade name Dantochlor®. The amount of the N-halohydantoin compound used in the recirculating water is broadly from 0.2 to 30 ppm, preferably from 0.5 to 5.0.

DETAILED DESCRIPTION OF THE INVENTION

The effective form of combined halogen can be generated: a) in situ by the addition of hydantoin to pulp slurries prior to or shortly after hypochlorite injection, b) by mixing DMH and free chlorine solutions prior to pulp slurry injection, or c) by direct feeding of halogenated hydantoins.

In addition to DMH, other N-hydrogen compounds, analogously to DMH, may be used. These include 5,5-dimethylhydantoin, glycouril, sulfamide, trisulfamide, p-toluene-sulfonamide, melamine, sodium triamidometaphosphate, 5,5-alkylhydantoins, methanesulfonamide, barbituric acid, 5-methyluracil, imidazoline, pyrrolidone, acetanilide, acetamide, N-ethylacetamide, phthalimide, benzamide, succinimide, cyanamide, urea, N-methylolurea, N-methylurea, acetylurea, biuret, methyl allophanate, methyl carbamate, phthalohydrazide, pyrrole, indole, formamide, N-methylformamide, dicyandiamide, ethyl carbamate, 1,3-dimethylbiuret, methyl phenyl biuret, 4,4-dimethyl-2-oxazolidinone, 6-methyluracil, 2-imidoazolidone, ethylene urea, 2-pyrimidone, N-ethylacetamide, azetidin-2-one, 2-pyrrolidone, caprolactam, phenyl sulfinimide, phenyl sulfinimidylamide, diphenyl sulfonimide, dimethyl sulfinimine, isothiazolene-1,1-dioxide, orthophosphoryl triamide, pyrophosphoryl triamide, phenyl phosphoryl-bis dimethyl amide, boric acid amide, hydantoin, and pyrrole. Expressly excluded is sulfamic acid, as its properties have been found to be inadequate for the purposes of the invention.

DMH and cyanuric acid enhance efficacy; however, the latter does not mitigate halogen consumption as well as DMH. While all N-hydrogen compounds (e.g., hydantoins, glycouril, sulfonamides, imides, oxazolidinones, amides, amino acids) appear to enhance free halogen efficacy and mitigate halogen consumption to varying degrees, the sulfamic acid described in U.S. Pat. No. 3,328,294 is clearly inferior to the compounds claimed herein. Hydantoins and cyanuric acid are preferred.

A wide variety of "free halogen sources" can be improved by applying the teaching of the instant invention. These include alkali metal and alkaline earth metal hypochlorites such as the lithium, sodium, potassium, calcium, and magnesium compounds, chlorine gas, bromine, bromine chloride, halogenated cyanurates such as trichlorcyanuric acid and sodium dichlorocyanurate, and dihalogenated hydantoins, and mixtures of such with sodium bromide.

The optimum amount of the N-hydrogen compound used is that needed to convert all free halogen to the combined form. This corresponds to a 1:1 molar ratio of halogen (based on the moles of free halogen) to hydantoin; however, concentrations as low as those producing a 2.6:1 halogen to DMH ratio have been shown to be effective. Any amount of N-hydrogen compound should provide some level of efficacy enhancement, while greater amounts of hydantoin do not reduce biocidal efficacy. A range corresponding to 0.1:1 to 10:1 halogen to N-hydrogen compound ratio broadly covers the invention. Halogen to DMH ratios of 0.1:1 to 10:1 correspond to hydantoin dosages of from 0.02 to 180 ppm.

Typically active halogen concentrations of 0.1–10 ppm as $Cl_2$ are employed in the pulp media. Amounts of 1 to 3 ppm are preferred.

To more fully describe the subject invention, attention is directed to the following examples:

EXAMPLE 1

The addition of 5,5-dimethylhydantoin (DMH) to sodium hypochlorite solutions enhances the biocidal activity of sodium hypochlorite. The conditions of this experiment were a modification of ASTM E 600-91. Two biocide solutions were evaluated: NaOCl and NaOCl mixed with DMH in a 0.25:1 molar ratio. The NaOCl and the DMH were mixed prior to pulp introduction. The biocides were introduced to the pulp slurry 10 minutes prior to inoculation with $2\times10^6$ cfu/ml P. Aeruginosa and E. Aerogenes. The pulp slurry consisted of 1.3% ground aspen wood pulp and 200 ppm rosin adjusted to pH=5.0–5.5 with aluminum sulfate. Bacteria populations were measured 3 hours after pulp slurry inoculation. Final total halogen concentrations were measured at the time of bacterial population plating by sample centrifuging followed by standard DPD analyses. Biocides were neutralized with sodium thiosulfate prior to plating. The results are set forth in Table 1:

TABLE 1

Effect of DMH on NaOCl/Bactericidal Efficacy

| System | Sample | Total Halogen: (ppm as $Cl_2$) Initial | Final | % Residual Halogen | Final Bacteria (cfu/ml) |
|---|---|---|---|---|---|
| NaOCl | A | 10 | 0.08 | 0.8 | $\leqq10^3$ |
| | B | 7.5 | 0.04 | 0.5 | $\leqq10^3$ |
| | C | 5.0 | 0.00 | 0 | $\leqq10^3$ |
| | D | 3.0 | 0.00 | 0 | $10^4$ |
| | E | 1.0 | 0.00 | 0 | $10^5$ |
| NaOCl:DMH (0.25:1 mole ratio) | F | 10 | 5.2 | 52 | $\leqq10^3$ |
| | G | 7.5 | 4.1 | 55 | $\leqq10^3$ |
| | H | 5.0 | 2.8 | 56 | $\leqq10^3$ |
| | I | 3.0 | 1.1 | 37 | $10^3$ |
| | J | 1.0 | 0.5 | 50 | $\leqq10^3$ |

DMH significantly enhanced the bactericidal efficacy of NaOCl. In the presence of DMH 1 ppm halogen produced bacteria reduction equivalent to that of 5 ppm halogen when used alone. This is a fivefold increase in efficacy.

DMH also reduced active halogen loss, reducing the predisposition for AOX formation. In the absence of DMH essentially all active halogen was consumed, while up to 56% remained when the DMH was present.

EXAMPLE 2

NaOCl efficacy was also enhanced by DMH upon NaOCl addition to DMH-treated slurries. Prereaction of DMH with NaOCl as described in Example 1 was not required. The conditions of this experiment were in other respects the same as Example 1. The molar ratio in the pulp slurry was 1:1 NaOCl to DMH. The results are reported in the table below:

TABLE 2

Effect of DMH-Treated Pulp on NaOCl/Bactericidal Efficacy

| System | Sample | Total Halogen: (ppm as $Cl_2$) Initial | Final | % Residual Halogen | Final Bacteria (cfu/ml) |
|---|---|---|---|---|---|
| NaOCl | A | 15 | 0.11 | 0.7 | $<10^3$ |
| | B | 10 | 0.04 | 0.4 | $<10^3$ |
| | C | 7.5 | 0.06 | 0.5 | $<10^3$ |
| | D | 5 | 0.02 | 0.4 | $10^4$ |
| | E | 3 | 0.00 | 0.0 | $10^5$ |
| NaOCl:DMH (1:1 mole ratio) | F | 1 | 0.00 | 0.0 | $10^6$ |
| | G | 15 | 1.88 | 12.5 | $<10^3$ |
| | H | 10 | 0.88 | 8.8 | $<10^3$ |
| | I | 7.5 | 0.41 | 5.5 | $<10^3$ |
| | J | 5 | 0.16 | 3.2 | $<10^4$ |
| | K | 3 | 0.05 | 1.7 | $10^4$ |
| | L | 1 | 0.00 | 0.0 | $10^4$ |

Again bactericidal efficacy was significantly increased by the presence of DMH. In the presence of DMH a 2 log reduction in bacteria concentration was achieved with an initial halogen concentration of 3 ppm, while 5 ppm was required in its absence: a twofold increase in efficacy.

The consumption of active halogen by the pulp medium was again mitigated by the presence of DMH.

EXAMPLE 3

DMH efficacy enhancement against preinoculated samples was also demonstrated. The conditions were the same as Example 1 except that the pulp was inoculated with bacteria 5 minutes prior to biocide introduction as opposed to 10 minutes after. Also the NaOCl to DMH mole ratio was increased from 0.25:1 to 1:1. The results are shown in Table 3:

TABLE 3

Effect of DMH on NaOCl Bactericidal Efficacy in Preinoculated Samples
Pulp Slurry Bactericidal Efficacy

| System | Total Halogen (ppm as $Cl_2$) Initial | Final | % Residual Halogen | Final Bacteria (cfu/ml) |
|---|---|---|---|---|
| NaOCl | 16.3 | 0.34 | 2.1 | $<10^3$ |
| | 3.4 | 0.03 | 1.0 | $<10^3$ |
| | 0.8 | 0.01 | 1.3 | $10^4$ |
| NaOCl:(1:1 mole ratio) | 15.0 | 3.6 | 24 | $<10^3$ |
| | 3.2 | 1.5 | 47 | $<10^3$ |
| | 0.8 | 0.3 | 38 | $10^3$ |

DMH again enhanced efficacy. In its presence a 3 log reduction was effected at a dosage of 0.8 ppm halogen (as compared to no reduction at 0.8 ppm in its absence). Active halogen consumption was again mitigated in the presence of DMH.

EXAMPLE 4

The effectiveness of DMH to mitigate halogen consumption was demonstrated at NaOCl to DMH molar ratios of 0.6:1 to 2.6:1. The experimental conditions were the same as those of Example 2, except that the pulp slurry was not inoculated with bacteria. The results are shown in the table below:

TABLE 4

Effect of NaOCl:DMH Molar ratio on Halogen Consumption

| NaOCl:DMH Mole Ratio | Total Halogen (ppm as $Cl_2$) Initial | Final | % Residual Halogen |
|---|---|---|---|
| 0 | 25.6 | 0.11 | 0.4 |
| 2.6:1 | 25.6 | 6.4 | 25 |
| 1.3:1 | 25.6 | 7.6 | 30 |
| 0.6:1 | 25.6 | 7.5 | 29 |

DMH concentrations as low as those producing NaOCl to DMH ratios of 2.6:1 reduced pulp slurry halogen consumption. As bactericidal efficacy of DMH treated systems was observed to correlate with residual total halogen concentration (see Examples 1 and 2), DMH is expected to enhance hypochlorite biocidal activity at DMH concentrations at least as low as those which provide NaOCl to DMH ratios of 2.6:1.

EXAMPLE 5

The activity of hydantoins was demonstrated to be greater than sulfamic acid and similar to cyanuric acid. The conditions were the same as those of Example 1. The molar ratio of the NaOCl to N-hydrogen compound was 1:1. The results are shown in Table 5:

TABLE 5

Effect of Cyanuric Acid, Sulfamic Acid and MEH on Bactericidal Efficacy

| System | Sample | Total Halogen (ppm as $Cl_2$) Initial | Final | % Residual Halogen | Final Bacteria (cfu/ml) |
|---|---|---|---|---|---|
| NaOCl | 5099:46 | 5.0 | 0.03 | 0.6 | $10^5$ |
| | A | 3.0 | 0.02 | 0.7 | $10^5$ |
| | B | 1.0 | 0.00 | 0.0 | $10^6$ |
| NaOCl:Sulfamic Acid | C | 5.0 | 3.8 | 76 | $10^5$ |
| | D | 3.0 | 2.5 | 83 | $10^5$ |
| | E | 1.0 | 0.6 | 60 | $10^6$ |
| NaOCl:Cyanuric Acid | F | 5.0 | 0.21 | 4.2 | $10^3$ |
| | G | 3.0 | 0.03 | 1.0 | $10^3$ |
| | H | 1.0 | 0.00 | 0.0 | $10^6$ |
| NaOCl:MEH | I | 5.0 | 2.4 | 48 | $10^3$ |
| | J | 3.0 | 0.2 | 7 | $10^4$ |
| | K | 1.0 | 0.03 | 3 | $10^5$ |

Sulfamic acid produced no efficacy enhancement over sodium hypochlorite alone. In contrast, 5-ethyl-5-methylhydantoin (MEH) dramatically increased NaOCl efficacy, providing a 3 log reduction at 5 ppm halogen as opposed to a 1 log reduction in its absence. Cyanuric acid provided similar efficacy enhancement to MEH.

Of the two components which provided efficacy enhancement, MEH and cyanuric acid, MEH provided the greatest mitigation of halogen decomposition; thus it is expected that MEH would provide the greatest reduction in AOX formation. In this aspect MEH would be preferred over cyanuric acid.

EXAMPLE 6

The conditions in this experiment were the same as in Example 1 except the initial total halogen concentration with respect to typical microbiological concentration was increased to about 70 ppm as $Cl_2$ to produce detectable levels of AOX. The results are shown in Table 6:

TABLE 6

Effluent AOX Analyses

| Composition | Initial Total Halogen (ppm as $Cl_2$) | Effluent AOX (ppm) |
|---|---|---|
| NaOCl | 74 | 5.8 |
| NaOCl:DMH | 69 | 3.7 |

DMH reduced the AOX of NaOCl-treated pulp slurry effluent by 36%.

EXAMPLE 7

This example shows the surprising efficacy of an N-halohydantoin compound as a bactericide as compared to the conventionally used sodium hypochlorite. Specifically, Dantochlor®, a commercial halogenated hydantoin containing predominantly dichlorodimethylhydantoin and dichlo roethylmethylhydantoin was used. The conditions were the same as those of Example 1. Table 7 shows the results:

TABLE 7

Efficacy of N-Halohydantoin Compound

| System | Sample | Total Halogen: (ppm as $Cl_2$) Initial | Final | % Residual Halogen | Final Bacteria (cfu/ml) |
|---|---|---|---|---|---|
| NaOCl | I | 7.5 | 0.05 | 1 | $\leqq 10^3$ |
| | J | 5.0 | 0.02 | 0.4 | $\leqq 10^3$ |
| Dantochlor | K | 3.0 | 0.00 | 0 | $10^4$ |
| | E | 7.5 | 4.2 | 56 | $\leqq 10^3$ |
| | F | 5.0 | 3.4 | 68 | $\leqq 10^3$ |
| | G | 3.0 | 1.1 | 36 | $\leqq 10^3$ |
| | H | 1.0 | 0.83 | 83 | $\leqq 10^3$ |

As can be seen from the data, Dantochlor showed a fivefold efficacy increase over sodium hypochlorite, providing a greater than 3 log reduction at 1 ppm initial halogen compared to 5 ppm for sodium hypochlorite. Additionally, the consumption of active halogen by the pulp medium was much less where the Dantochlor was used relative to sodium hypochlorite.

What is claimed is:

[1. A method of enhancing the efficacy of a free halogen-generating slimicide and reducing organic halogen by-products in an organic matter-containing circulating water system which comprises adding an N-hydrogen compound selected from the group consisting of p-toluenesulfonamide, dimethylhydantoin, methylethylhydantoin, cyanuric acid, succinimide, urea, 4,4-dimethyl-2-oxazolidinone, and glycouril, directly to said system before or after the addition of the slimicide or with said slimicide in a mixture consisting essentially of the slimicide and said compound; wherein the N-hydrogen compound is added at a ratio sufficient to maintain a 0.1:1 to 10:1 mole ratio of slimicide to N-hydrogen compound in the circulating system, wherein at least 0.2 weight percent of said organic matter is present in said system, wherein the slimicide is chlorine gas, bromine, bromine chloride, an alkali metal or alkaline earth metal hypohalite, a halogenated hydantoin, a halogenated cyanurate, or halogenated cyanuric acid, and wherein said mixture of the N-hydrogen compound and the slimicide is present in said system in a slimicidally effective amount.]

2. The method of claim 1 wherein the mixture of the slimicide and the N-hydrogen compound is formed just prior to the addition to said circulating water system.

3. The method of claim 1 wherein the slimicide is chlorine gas or sodium hypochlorite.

4. The method of claim 1 wherein from 0.1 to 10 ppm of active slimicide (expressed as $Cl_2$) is maintained in the circulating water system.

[5. The method of claim 1 wherein the circulating water system is used in pulp and paper processing or oil field applications.]

[6. The method of claim 1 wherein said organic matter is present in said system at from about 0.5 to about 3 weight percent.]

[7. The method of claim 1 wherein said organic matter is from about 95 to about 99 percent wood fiber.]

8. The method of claim 1 wherein said slimicide is a halogenated hydantoin of the formula:

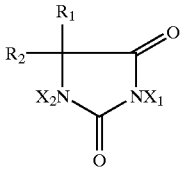

wherein $R_1$ and $R_2$ are independently selected from the group consisting of lower alkyl having 1 to 12 carbon atoms, and wherein $X_1$ and $X_2$ are independently selected from the group consisting of bromine, chlorine and hydrogen, and at least one of $X_1$ and $X_2$ being bromine or chlorine.

[9. The method of claim 8 wherein said organic matter is from about 95 to about 99 percent wood fiber.]

[10. The method of claim 8 wherein said organic matter is present in said system at from about 0.5 to about 3 weight percent.]

11. The method of claim 8 wherein the halogenated hydantoin contains bromochlorodimethylhydantoin.

12. The method of claim 8 wherein the halogenated hydantoin is a mixture of dichlorodimethylhydantoin and dichloroethylmethylhydantoin.

[13. A method of enhancing the efficacy of a free halogen-generating slimicide and reducing organic halogen by-products in an organic matter-containing circulating water system which comprises adding an N-hydrogen compound selected from the group consisting of p-toluenesulfonamide dimethylhydantoin, methylethylhydantoin, cyanuric acid, succinimide, urea, 4,4-dimethyl-2-oxazolidinone, and glycouril, directly to said system before or after the addition of the slimicide or with said slimicide in a mixture consisting essentially of the slimicide and said compound; wherein the N-hydrogen compound is added at a ratio sufficient to maintain a 0.1:1 to 10:1 mole ratio of slimicide to N-hydrogen compound in the circulating system; and wherein at least 0.2 weight percent of said organic matter is present in said system, wherein said slimicide is a halogenated hydantoin of the formula:

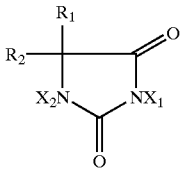

wherein $R_1$ and $R_2$ are independently selected from the group consisting of lower alkyl having 1 to 12 carbon atoms, wherein $X_1$ and $X_2$ are independently selected from the group consisting of bromine and chlorine, and wherein the mixture of the N-hydrogen compound and the slimicide is present in said system in a slimicidally effective amount.]

*14. In a process for making paper from pulp fiber wherein from 0.2 to 3 weight percent of organic matter comprising from 95 to 99 weight percent pulp fiber is maintained in a circulating water slurry in the presence of sizing, the improvement of performing said process in the presence of a slimicidally effective amount of an N-hydrogen compound and a slimicide in a molar ratio of from 0.1:1 to 10:1 in said circulating water slurry; wherein said N-hydrogen compound is p-toluenesulfonamide, dimethylhydantoin, methylethylhydantoin, cyanuric acid, succinimide, urea, 4,4-dimethyl-2-oxazolidinone, or glycouril and said slimicide is*

*chlorine gas, bromine, bromine chloride, an alkali metal or alkaline earth metal hypohalite, a halogenated hydantoin, a halogenated cyanurate, or halogenated cyanuric acid and the amount of the N-hydrogen compound present in said circulating water slurry is sufficient to enhance the biocidal efficacy of the slimicide and reduce absorbable organic halogen (AOX) by-product formation, wherein the N-hydrogen compound is directly added to the slurry before or after the addition of the slimicide or with the slimicide in a mixture consisting essentially of the slimicide and the N-hydrogen compound.*

*15. The papermaking process of claim 14 wherein the slurry is at a pH of from about 5.0 to 5.5.*

*16. In a process for making paper from pulp fiber wherein from 0.2 to 3 weight percent of organic matter comprising from 95 to 99 weight percent pulp fiber is maintained in a circulating water slurry in the presence of sizing, the improvement of performing said process in the presence of a slimicidally effective amount of an N-hydrogen compound and a slimicide in a molar ratio of from 0.1:1 to 10:1 in said circulating water slurry; wherein said N-hydrogen compound is p-toluenesulfonamide, dimethylhydantoin, methylethylhydantoin, cyanuric acid, succinimide, urea, 4,4-dimethyl-2-oxazolidinone, or glycouril and said slimicide is a halogenated hydantoin of the formula*

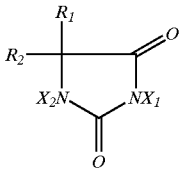

*wherein $R_1$ and $R_2$ are independently selected from the group consisting of lower alkyl having 1 to 12 carbon atoms, wherein $X_1$ and $X_2$ are independently selected from the group consisting of bromine and chlorine, and the amount of the N-hydrogen compound present in said circulating water slurry is sufficient to enhance the biocidal efficacy of the slimicide and reduce absorbable organic halogen (AOX) by-product formation, wherein the N-hydrogen compound is directly added to the slurry before or after the addition of the slimicide or with the slimicide in a mixture consisting essentially of the slimicide and the N-hydrogen compound.*

* * * * *

UNITED STATES PATENT AND TRADEMARK OFFICE

CERTIFICATE OF CORRECTION

PATENT NO. : RE39,021 E
APPLICATION NO. : 10/044594
DATED : March 21, 2006
INVENTOR(S) : Philip G. Sweeny It is certified that error appears in the above-identified patent and that said Letters Patent is hereby corrected as shown below:

Column 7, line 51:

Claim 2:

Now reads: "The method of claim 1 wherein..."

Should read: -- The papermaking process of claim 14 wherein --

Column 7, line 54:

Claim 3:

Now reads: "The method of claim 1 wherein..."

Should read: -- The papermaking process of claim 14 wherein --

Column 7, line 56:

Claim 4:

Now reads: "The method of claim 1 wherein..."

Should read: -- The papermaking process of claim 14 wherein --

Column 8, line 1:

Claim 8:

Now reads: "The method of claim 1 wherein..."

Should read: -- The papermaking process of claim 14 wherein --

Signed and Sealed this
Twenty-sixth Day of April, 2011

David J. Kappos

David J. Kappos
*Director of the United States Patent and Trademark Office*